United States Patent
Hasegawa

(10) Patent No.: US 11,704,826 B2
(45) Date of Patent: Jul. 18, 2023

(54) DIAGNOSTIC IMAGING SUPPORT APPARATUS CAPABLE OF AUTOMATICALLY SELECTING AN IMAGE FOR EXTRACTING A CONTOUR FROM AMONG A PLURALITY OF IMAGES OF DIFFERENT TYPES, DIAGNOSTIC IMAGING SUPPORT METHOD THEREFOR, AND NON-TRANSITORY RECORDING MEDIUM FOR STORING DIAGNOSTIC IMAGING SUPPORT PROGRAM THEREFOR

(71) Applicant: FUJIFILM Corporation, Tokyo (JP)

(72) Inventor: Yu Hasegawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 255 days.

(21) Appl. No.: 17/103,964

(22) Filed: Nov. 25, 2020

(65) Prior Publication Data

US 2021/0082139 A1    Mar. 18, 2021

Related U.S. Application Data

(63) Continuation of application No. PCT/JP2019/021081, filed on May 28, 2019.

(30) Foreign Application Priority Data

Jun. 7, 2018   (JP) ................................ 2018-109652

(51) Int. Cl.
*G06T 7/13*    (2017.01)
*G06T 7/64*    (2017.01)
(Continued)

(52) U.S. Cl.
CPC .............. *G06T 7/64* (2017.01); *A61B 6/5217* (2013.01); *G06T 5/50* (2013.01); *G06T 7/0012* (2013.01);
(Continued)

(58) Field of Classification Search
CPC .... G06T 7/64; G06T 5/50; G06T 7/0012; G06T 7/13; G06T 2207/10081;
(Continued)

(56) References Cited

U.S. PATENT DOCUMENTS

2006/0099558 A1*   5/2006   Ema .................... G06T 15/08
                                                                     434/262
2012/0076419 A1   3/2012   Kono et al.
(Continued)

FOREIGN PATENT DOCUMENTS

JP      H1128252      2/1999
JP      2005106507    4/2005
(Continued)

OTHER PUBLICATIONS

"International Search Report (Form PCT/ISA/210) of PCT/JP2019/021081," dated Aug. 20, 2019, with English translation thereof, pp. 1-5.

(Continued)

*Primary Examiner* — Siamak Harandi
(74) *Attorney, Agent, or Firm* — JCIPRNET

(57) ABSTRACT

With a diagnostic imaging support apparatus, a diagnostic imaging support method, and a diagnostic imaging support program, an optimum image for extracting a contour can be automatically selected from a superimposed image obtained by superimposing a plurality of images of different types. A diagnostic imaging support apparatus 1 includes: an accepting unit 22 that accepts a specification of the position of a predetermined defined region R on a superimposed image G obtained by superimposing a plurality of images of different types including a target image G0 that is a target on which a contour is created; a selection unit 23 that selects an image for extracting a contour on the basis of image information about regions R0, R1, and R2, in the plurality of images of
(Continued)

different types, each corresponding to the accepted defined region R; and a contour extraction unit 24 that extracts the contour from the selected image.

20 Claims, 4 Drawing Sheets

(51) Int. Cl.
*A61B 6/00* (2006.01)
*G06T 5/50* (2006.01)
*G06T 7/00* (2017.01)
*A61B 5/055* (2006.01)
*A61B 6/03* (2006.01)

(52) U.S. Cl.
CPC ............... *G06T 7/13* (2017.01); *A61B 5/055* (2013.01); *A61B 6/032* (2013.01); *A61B 6/037* (2013.01); *G06T 2207/10081* (2013.01); *G06T 2207/10088* (2013.01); *G06T 2207/10104* (2013.01); *G06T 2207/20221* (2013.01); *G06T 2207/30004* (2013.01)

(58) Field of Classification Search
CPC . G06T 2207/10088; G06T 2207/10104; G06T 2207/20221; G06T 2207/30004; G06T 2200/04; G06T 2207/30096; G06T 7/174; A61B 6/5217; A61B 5/055; A61B 6/032; A61B 6/037; A61B 5/4887; A61B 5/0037; A61B 2576/00; A61B 6/5223; A61B 6/5235; A61B 6/5241; A61B 6/5247; A61B 6/469; G01T 1/161
See application file for complete search history.

(56) References Cited

U.S. PATENT DOCUMENTS

2014/0303486 A1* 10/2014 Baumgartner ......... A61B 5/055
600/414
2015/0363979 A1    12/2015 Takano et al.
2016/0192832 A1*  7/2016 Kamiyama ........... G06T 7/0012
382/128

FOREIGN PATENT DOCUMENTS

| JP | 2012192137 | 10/2012 |
| JP | 2014064957 | 4/2014 |
| JP | 2014155207 | 8/2014 |
| JP | 5683888 | 3/2015 |

OTHER PUBLICATIONS

"Written Opinion of the International Searching Authority (Form PCT/ISA/237) of PCT/JP2019/021081," dated Aug. 20, 2019, with English translation thereof, pp. 1-7.
"Office Action of Japan Counterpart Application", dated Feb. 22, 2022, with English translation thereof, pp. 1-5.
"Office Action of Japan Counterpart Application" with English translation thereof, dated Oct. 12, 2021, p. 1-p. 4.

* cited by examiner

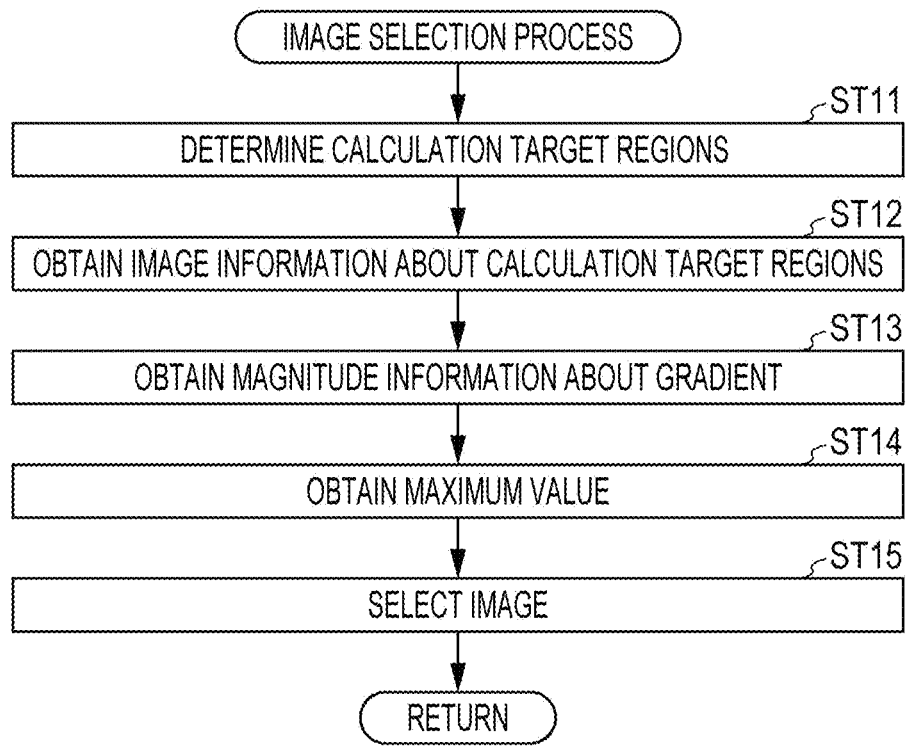
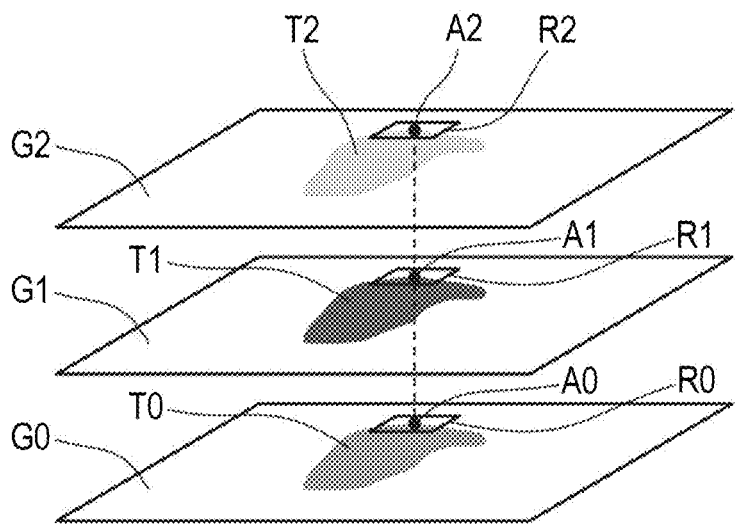

DIAGNOSTIC IMAGING SUPPORT APPARATUS CAPABLE OF AUTOMATICALLY SELECTING AN IMAGE FOR EXTRACTING A CONTOUR FROM AMONG A PLURALITY OF IMAGES OF DIFFERENT TYPES, DIAGNOSTIC IMAGING SUPPORT METHOD THEREFOR, AND NON-TRANSITORY RECORDING MEDIUM FOR STORING DIAGNOSTIC IMAGING SUPPORT PROGRAM THEREFOR

CROSS-REFERENCE TO RELATED APPLICATIONS

This application is a Continuation of PCT International Application No. PCT/JP2019/021081 filed on May 28, 2019, which claims priority under 35 U.S.C § 119(a) to Japanese Patent Application No. 2018-109652 filed on Jun. 7, 2018. Each of the above application(s) is hereby expressly incorporated by reference, in its entirety, into the present application.

BACKGROUND OF THE INVENTION

1. Field of the Invention

The present disclosure relates to a diagnostic imaging support apparatus, a diagnostic imaging support method, and a non-transitory computer readable recording medium storing a diagnostic imaging support program.

2. Description of the Related Art

Currently, radiation treatment is known as a method for treating, for example, cancer. In radiation treatment, it is desirable that normal organs be exposed to lower doses of radiation to the extent possible and cancer and organs at risk, which are targets, be exposed to higher doses of radiation. Therefore, radiographic images, such as CT (computed tomography) images, are first obtained, doctors, radiologists, etc. use the obtained radiographic images to make a treatment plan in which the direction of radiation and the dose of radiation are determined, and the affected part is subjected to radiation treatment. To make a treatment plan, computer simulation needs to be carried out. For this, on the radiographic images, the regions of cancer and organs at risk, which are targets, need to be outlined with contours. In general, the dose of radiation to which an affected part is exposed in radiation treatment is higher than the dose of radiation used at the time of imaging performed to obtain radiographic images for diagnoses. Therefore, in order to appropriately control the dose of radiation in radiation treatment, contours as described above need to be precisely created.

For example, in a case where the contour of a tumor region on a CT image is to be created, images having different characteristics, such as an MR (magnetic resonance) image and a PET (positron emission tomography) image, from which a region that is a target can be easily extracted are aligned and superimposed on the CT image to thereby determine the contour of the target region and extract the contour.

JP2014-64957A describes a form in which the same target in a living body is imaged to obtain a CT image and an MR image, a contour is extracted from one of the images, and the other image, which is used as a tissue image, is rearranged within the contour extracted from the one image.

SUMMARY OF THE INVENTION

When the contour of a region that is a target is extracted from a superimposed image obtained by aligning a plurality of images of different types, currently, an operator, such as a radiologist, manually selects an image from which the contour is to be extracted, in accordance with a tumor and an organ at risk that are targets, and therefore, the selected image may differ depending on the operator or selection may take time. In the method described in JP2014-64957A mentioned above, a technique for automatically selecting an image suitable to creation of a contour from among a plurality of images of different types is not disclosed.

The present disclosure has been made in view of the above-described circumstances, and an object thereof is to enable automatic selection of an optimum image for extracting a contour, from a superimposed image obtained by superimposing a plurality of images of different types.

A diagnostic imaging support apparatus of the present disclosure includes: an accepting unit that accepts a specification of a position of a predetermined defined region on a superimposed image obtained by superimposing a plurality of images of different types including a target image that is a target on which a contour is created;
a selection unit that selects an image for extracting a contour on the basis of image information about regions, in the plurality of images of different types, each corresponding to the defined region accepted by the accepting unit; and
a contour extraction unit that extracts the contour from the image selected by the selection unit.

Here, in the present disclosure, for example, a CT image obtained while a contrast medium is injected into a subject and a CT image obtained without injecting a contrast medium into the subject are the same CT images but are assumed to be "images of different types". That is, images obtained by imaging under any different imaging conditions are assumed to be "images of different types". Further, images obtained on the basis of different imaging principles, such as a CT image, an MR image, and a PET image, are assumed to be "images of different types".

The diagnostic imaging support apparatus of the present disclosure may further include an image processing unit that reflects contour information about the contour extracted by the contour extraction unit on the target image to create a contour.

In the diagnostic imaging support apparatus of the present disclosure, the selection unit may select on the basis of magnitude information about a gradient obtained from the image information, an image in which the gradient is largest.

In the diagnostic imaging support apparatus of the present disclosure, the selection unit may obtain the magnitude information about the gradient from image information about each pixel in the regions, in the plurality of images of different types, each corresponding to the defined region, obtain a maximum value from the magnitude information about the gradient of each pixel for each of the plurality of images of different types, and select an image for which the obtained maximum value is largest from among the plurality of images.

In the diagnostic imaging support apparatus of the present disclosure, the accepting unit may change a size of the defined region on the basis of a type of an imaging target in the plurality of images of different types.

In the diagnostic imaging support apparatus of the present disclosure, the plurality of images of different types may be a plurality of images obtained under different imaging conditions. In this case, the plurality of images of different types can be images of one type, which are CT images, MR images, or PET images.

Here, in the present disclosure, "imaging conditions" mean various conditions applied at the time of imaging, such as whether a contrast medium is injected into the subject, X-ray irradiation conditions, and the slice increment.

In the diagnostic imaging support apparatus of the present disclosure, the plurality of images of different types may be a plurality of images obtained on the basis of different imaging principles. In this case, the plurality of images of different types can be images of two or more types among a CT image, an MR image, and a PET image.

In the diagnostic imaging support apparatus of the present disclosure, the plurality of images of different types may be a plurality of images obtained under different imaging conditions and a plurality of images obtained on the basis of different imaging principles. In this case, the plurality of images of different types can be images of two or more types among a CT image, an MR image, and a PET image.

Here, in the present disclosure, "imaging principles" mean imaging methods that are used when imaging, such as CT imaging, MR imaging, and PET imaging, is performed.

In the diagnostic imaging support apparatus of the present disclosure, the target image may be a CT image.

In the diagnostic imaging support apparatus of the present disclosure, the plurality of images of different types may be cross-sectional images in a same direction.

Here, in the present disclosure, the "same direction" is not limited to directions that completely coincide with each other but includes directions that vary within an allowable range.

A diagnostic imaging support method of the present disclosure includes: accepting a specification of a position of a predetermined defined region on a superimposed image obtained by superimposing a plurality of images of different types including a target image that is a target on which a contour is created;

selecting an image for extracting a contour on the basis of image information about regions, in the plurality of images of different types, each corresponding to the accepted defined region; and extracting the contour from the selected image.

A non-transitory computer readable recording medium storing a diagnostic imaging support program of the present disclosure causes a computer to perform a process including: a step of accepting a specification of a position of a predetermined defined region on a superimposed image obtained by superimposing a plurality of images of different types including a target image that is a target on which a contour is created;

a step of selecting an image for extracting a contour on the basis of image information about regions, in the plurality of images of different types, each corresponding to the accepted defined region; and a step of extracting the contour from the selected image.

Another diagnostic imaging support apparatus according the present disclosure includes: a memory that stores an instruction to be executed by a computer; and a processor configured to execute the stored instruction, the processor performing a process of accepting a specification of a position of a predetermined defined region on a superimposed image obtained by superimposing a plurality of images of different types including a target image that is a target on which a contour is created, selecting an image for extracting a contour on the basis of image information about regions, in the plurality of images of different types, each corresponding to the accepted defined region, and extracting the contour from the selected image.

In the present disclosure, a process of accepting a specification of the position of a predetermined defined region on a superimposed image obtained by superimposing a plurality of images of different types including a target image that is a target on which a contour is created; selecting an image for extracting a contour on the basis of image information about regions, in the plurality of images of different types, each corresponding to the accepted defined region; and extracting the contour from the selected image is performed. Accordingly, an optimum image for extracting a contour can be automatically selected from the superimposed image obtained by superimposing the plurality of images. Therefore, a contour can be precisely and efficiently created on the basis of the features of the respective images.

BRIEF DESCRIPTION OF THE DRAWINGS

FIG. 5 is a flowchart illustrating an image selection process performed in the embodiment of the present disclosure;

FIG. 6 is a diagram for describing selection of an image;

DESCRIPTION OF THE PREFERRED EMBODIMENTS

Figure 1:
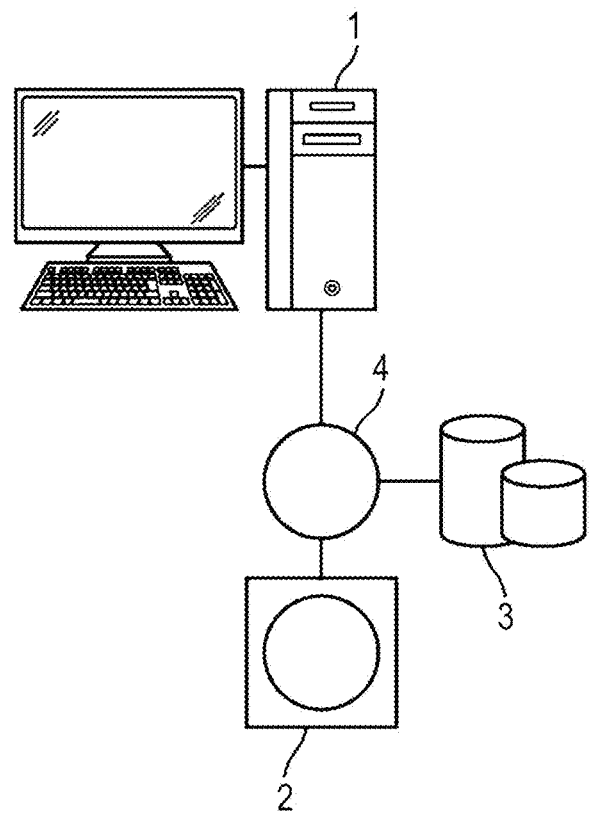
FIG. 1 is a hardware configuration diagram illustrating the overview of a diagnostic support system to which a diagnostic imaging support apparatus according to an embodiment of the present disclosure is applied.

Hereinafter, an embodiment of the present disclosure will be described with reference to the drawings. FIG. 1 is a hardware configuration diagram illustrating the overview of a diagnostic support system to which a diagnostic imaging support apparatus according to the embodiment of the present disclosure is applied. As illustrated in FIG. 1, in the diagnostic support system, a diagnostic imaging support apparatus 1 according to this embodiment, a three-dimensional imaging apparatus 2, and an image storage server 3 are connected so as to enable communication via a network 4. In the diagnostic support system, a process of obtaining a plurality of images that are obtained by imaging a patient who is a target for which a radiation treatment plan is to be made and that includes a target image, which is a target on which a contour is created, and selecting from among the plurality of obtained images, an image for extracting a contour is performed.

The three-dimensional imaging apparatus 2 is an apparatus that images an area, which is a diagnostic target, of a subject to generate a three-dimensional image representing the area. Specifically, the three-dimensional imaging apparatus 2 is, for example, a CT apparatus, an MR apparatus, or a PET apparatus. The three-dimensional image generated by the three-dimensional imaging apparatus 2 is transmitted to the image storage server 3 and saved. Note that this embodiment assumes that the three-dimensional imaging apparatus 2 is a CT apparatus and that a three-dimensional image formed of a plurality of cross-sectional of a subject is generated. In this embodiment, a cross-sectional corresponds to a target image.

The image storage server 3 is a computer that saves and manages various types of data, and includes an external mass storage device and database management software. The image storage server 3 communicates with the other apparatuses via the network 4 by wire or wirelessly to transmit and receive image data, etc. Specifically, the image storage server 3 receives image data of a three-dimensional image, etc. generated by the three-dimensional imaging apparatus 2 via the network, and saves the image data in a recording medium, such as the external mass storage device, to manage the image data. Note that the form of storage of image data and communication between the apparatuses via the network 4 conform to a protocol, such as DICOM (Digital Imaging and COmmunication in Medicine). In this embodiment, a plurality of three-dimensional images of different types, which include, for example, a CT image, an MR image, and a PET image, of the same subject and cross-sectional images that form the three-dimensional images are saved in the image storage server 3.

The diagnostic imaging support apparatus 1 is implemented as one computer in which the diagnostic imaging support program of the present disclosure is installed. The computer may be a workstation or a personal computer that is directly operated by a doctor who makes a diagnosis or may be a server computer that is connected to the workstation or personal computer via a network. The diagnostic imaging support program is recorded to a recording medium, such as a DVD (digital versatile disc) or a CD-ROM (compact disc read-only memory), distributed, and installed in the computer from the recording medium. Alternatively, the diagnostic imaging support program is stored in a storage device of the server computer connected to the network or in a network storage so as to be externally accessible, downloaded to the computer that is used by a doctor in response to a request, and installed.

Figure 2:
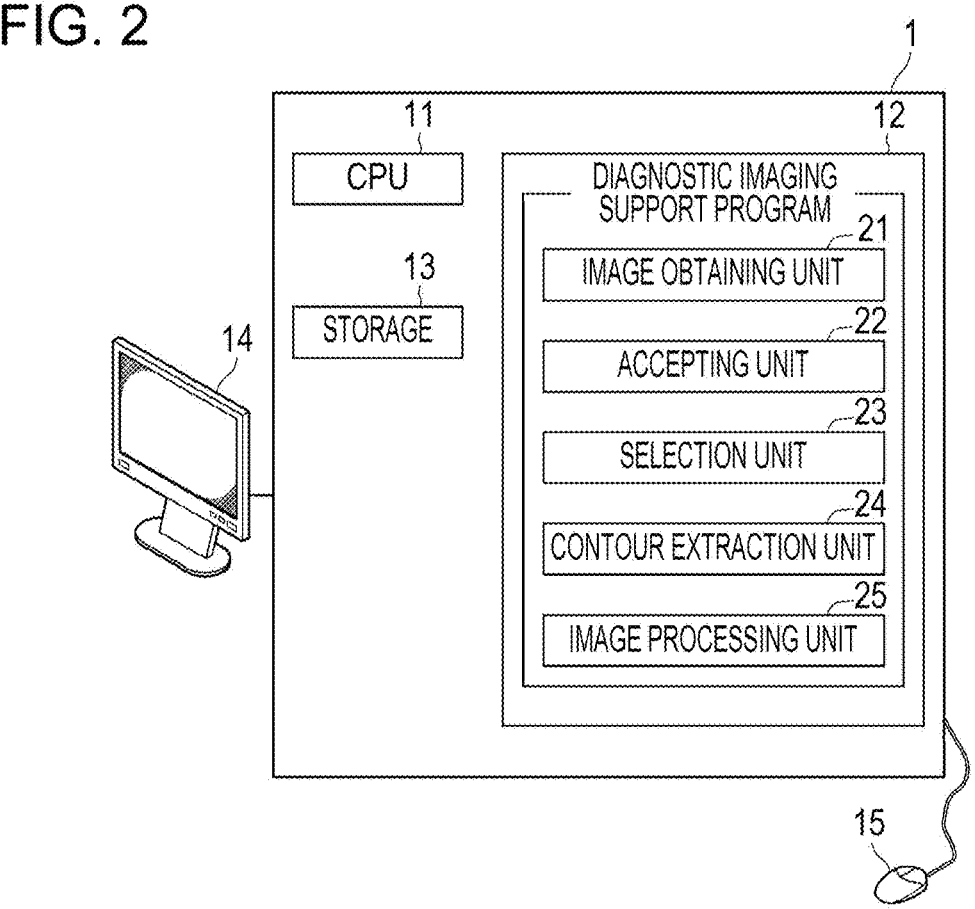
FIG. 2 is a diagram illustrating an overall configuration of the diagnostic imaging support apparatus.

FIG. 2 is a diagram illustrating an overall configuration of the diagnostic imaging support apparatus 1 implemented by installing the diagnostic imaging support program in the computer. As illustrated in FIG. 2, the diagnostic imaging support apparatus 1 includes a CPU (central processing unit) 11, a memory 12, and a storage 13 as in a typical configuration of workstations. To the diagnostic imaging support apparatus 1, a display 14, which is, for example, a liquid crystal display, and an input unit 15, which includes, for example, a keyboard and a mouse, are connected.

The storage 13 is formed of a storage device, such as a hard disk or an SSD (solid state drive). In the storage 13, various types of information including three-dimensional images of subjects and information necessary for processing obtained from the image storage server 3 via the network 4 is stored.

In the memory 12, the diagnostic imaging support program is stored. The diagnostic imaging support program defines, as processing to be performed by the CPU 11, an obtaining process of obtaining from the image storage server 3 a plurality of images of different types including a target image, which is a target on which a contour is created, an accepting process of accepting a specification of the position of a predetermined defined region on a superimposed image obtained by superimposing the plurality of images of different types including the target image, which is a target on which a contour is created, a selection process of selecting, on the basis of image information about regions, in the plurality of images, each corresponding to the accepted defined region, an image for extracting a contour, a contour extraction process of extracting the contour from the selected image, and an image processing process of reflecting contour information about the extracted contour on the target image to create a contour.

When the CPU 11 performs these processes in accordance with the program, the computer functions as an image obtaining unit 21, an accepting unit 22, a selection unit 23, a contour extraction unit 24, and an image processing unit 25. Note that in this embodiment, the functions of the units are executed by the diagnostic imaging support program; however, the present disclosure is not limited to this, and the functions of the units may be executed by a combination of, for example, a plurality of ICs (integrated circuits), processors, ASICs (application-specific integrated circuits), or FPGAs (field-programmable gate arrays), memory, etc. as appropriate.

The image obtaining unit 21 obtains from the image storage server 3 a plurality of images of different types including a target image, which is a target on which a contour is created. Here, the images obtained by the image obtaining unit 21 are cross-sectional images each forming a three-dimensional image of the corresponding type. The cross-sectional images are cross-sectional images in the same direction. Note that in a case where the plurality of images of different types have already been stored in the storage 13, the image obtaining unit 21 may obtain the plurality of images from the storage 13.

Regarding the plurality of images of different types described above, for example, a CT image obtained while a contrast medium is injected into a subject and a CT image obtained without injecting a contrast medium into the subject are the same CT images but are assumed to be "images of different types". That is, images obtained by imaging under any different imaging conditions are assumed to be "images of different types". Further, images obtained on the basis of different imaging principles, such as a CT image, an MR image, and a PET image, are assumed to be "images of different types".

Among the plurality of images, the target image may be a CT image and the images of different types may be images of one type, namely, CT images, MR images, or PET images. For example, in a case where the images of different types are CT images, the plurality of images are three CT images, namely, the CT image that is a target image and two CT images obtained under imaging condition 1 and imaging condition 2 different from that for the CT image that is a target image. In a case where the images of different types are MR images, the plurality of images are three images, namely, the CT image that is a target image and two MR images obtained under imaging condition 1 and imaging condition 2, which are different conditions. In a case where the images of different types are PET images, the plurality of images are three images, namely, the CT image that is a target image and two PET images obtained under imaging condition 1 and imaging condition 2, which are different conditions. Note that the number of the plurality of images is not limited to three and can be changed as appropriate.

Among images of different types, the target image may be a CT image and the images of different types may be images of two or more types among a CT image, an MR image, and a PET image. For example, in a case where the images of different types are a CT image and an MR image, the plurality of images are three images, namely, the CT image that is a target image, a CT image obtained under an imaging condition different from that for the CT image that is a target image, and an MR image. In a case where the images of different types are a CT image and a PET image, the plurality of images are three images, namely, the CT image that is a target image, a CT image obtained under an imaging condition different from that for the CT image that is a target image, and a PET image. In a case where the images of different types are an MR image and a PET image, the plurality of images are three images, namely, the CT image that is a target image, an MR image, and a PET image. Note that the number of the plurality of images is not limited to three and can be changed as appropriate.

In this embodiment, for example, the images of different types are images of different types obtained for the same subject, and specifically, the image obtaining unit 21 obtains a CT image G0, which is a target image on which a contour is created, an MR image G1, and a PET image G2 from the image storage server 3. Here, the images obtained by the image obtaining unit 21 are cross-sectional images each forming a three-dimensional image of the corresponding type. The cross-sectional images are cross-sectional images in the same direction. Note that in a case where the CT image G0, the MR image G1, and the PET image G2 have already been stored in the storage 13, the image obtaining unit 21 may obtain the CT image G0, the MR image G1, and the PET image G2 from the storage 13.

The accepting unit 22 accepts a specification of the position of a predetermined defined region R on a superimposed image G obtained by superimposing the plurality of images of different types including the target image obtained by the image obtaining unit 21. Note that the superimposed image G is an image obtained by aligning and superimposing the CT image G0, the MR image G1, and the PET image G2.

Figure 3:
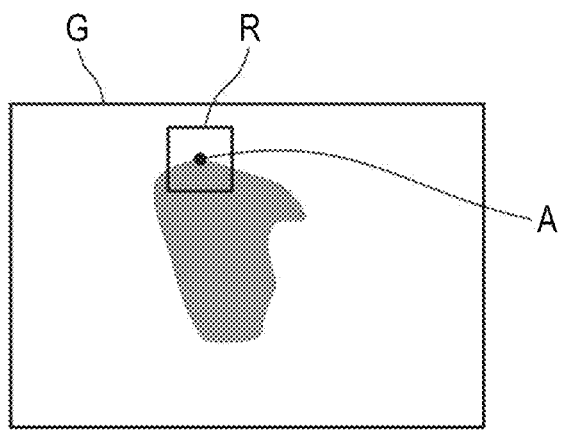
FIG. 3 is a diagram for describing a specification of a position on a superimposed image.

FIG. 3 is a diagram for describing a specification of a position on a superimposed image. Specifically, on the superimposed image G displayed on the display 14, an operator uses the input unit 15 to move a cursor A displayed on the display 14 to a position desired by the operator, that is, to a position near the contour of a target region that the operator wants to extract, and fix the position of the cursor A. The defined region R having a predetermined size is stored in the storage 13, and the accepting unit 22 accepts a region that surrounds the cursor A as the predetermined defined region R in which the center of the predetermined defined region R corresponds to the position of the cursor A. This embodiment assumes that the predetermined defined region R is a region of 5×5 pixels. Note that the size and/or shape of the predetermined defined region R can be changed by the operator as desired.

The selection unit 23 selects an image for extracting a contour, on the basis of image information about regions, in the plurality of images of different types, each corresponding to the predetermined defined region R accepted by the accepting unit 22. Note that the method of selecting an image by the selection unit 23 will be described in detail below.

The contour extraction unit 24 extracts a contour from the image selected by the selection unit 23. Note that the method of extracting a contour by the contour extraction unit 24 will be described in detail below.

The image processing unit 25 reflects contour information about the contour extracted by the contour extraction unit 24 on the CT image G0, which is a target image, to create a contour. Note that the method of creating a contour will be described in detail below. In this embodiment, the image processing unit 25 also functions as a processing unit that generates the superimposed image G obtained by aligning and superimposing the CT image G0, the MR image G1, and the PET image G2. The images can be aligned by using a known aligning technique, such as an affine transformation. The alignment may be manually performed by the operator or automatically performed by the image processing unit 25. For the superimposed image G, the image processing unit 25 superimposes the CT image G0, the MR image G1, and the PET image G2 in accordance with light transmittances determined in advance for the respective images. Note that the light transmittances are saved in advance in the storage 13 for the respective types of images and can be changed by the operator as desired.

Figure 4:
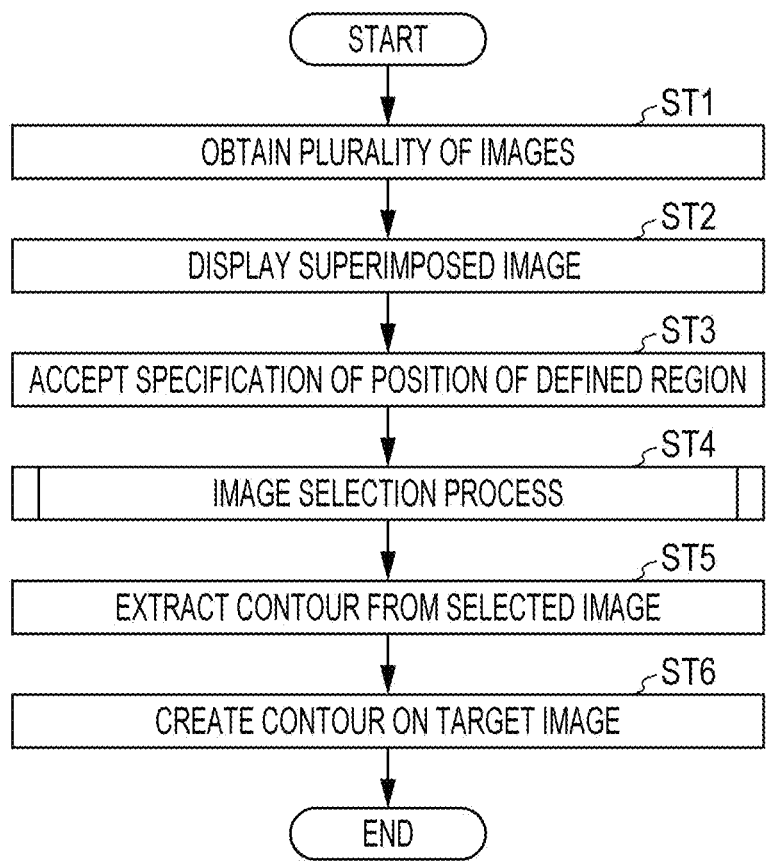
FIG. 4 is a flowchart illustrating processing performed in the embodiment of the present disclosure.

Now, processing performed in this embodiment is described. FIG. 4 is a flowchart illustrating the processing performed in this embodiment.

First, the image obtaining unit 21 obtains the CT image G0, the MR image G1, and the PET image G2 as a plurality of images of different types (step ST1). Next, the image processing unit 25 generates the superimposed image G by superimposing the CT image G0, the MR image G1, and the PET image G2, and a display control unit (not illustrated) displays the superimposed image G on the display 14 (step ST2).

Next, the accepting unit 22 accepts a specification of the position of the predetermined defined region R as described above (step ST3), and the selection unit 23 performs a selection process of selecting an image for extracting a contour (step ST4). FIG. 5 is a flowchart illustrating the image selection process performed in this embodiment.

As illustrated in FIG. 5, the selection unit 23 first determines calculation target regions that are calculation targets for selecting an image (step ST11). FIG. 6 is a diagram for describing selection of an image.

In the CT image G0, the MR image G1, and the PET image G2 obtained by the image obtaining unit 21, the selection unit 23 determines regions each corresponding to the predetermined defined region R accepted by the accepting unit 22 to be calculation target regions.

As illustrated in FIG. 6, in the CT image G0, the selection unit 23 sets a position corresponding to the position of the cursor A specified on the superimposed image G as a specified position A0 and sets a region corresponding to the predetermined defined region R set on the superimposed image G as a calculation target region R0. Note that a region T0 in the CT image G0 is the region T0 that represents a tumor and an organ at risk that are targets of irradiation.

In the MR image G1 and the PET image G2, the selection unit 23 sets a specified position A1, a specified position A2, a calculation target region R1, and a calculation target region R2 as illustrated in FIG. 6 as in the CT image G0. Note that regions T1 and T2 in the MR image G1 and the PET image G2 are the regions T1 and T2 each representing a tumor and an organ at risk that are targets of irradiation. Note that in this embodiment, the selection unit 23 sets the specified positions A0, A1, and A2 and the calculation target regions R0, R1, and R2 as described above; however, the present disclosure is not limited to this, and the selection unit 23 may set only the calculation target regions R0, R1, and R2.

Next, the selection unit 23 obtains image information about the calculation target regions R0, R1, and R2 (step ST12). Specifically, the selection unit 23 obtains the pixel value of each pixel in each of the calculation target regions R0, R1, and R2 as image information. Subsequently, the selection unit 23 obtains from the obtained pixel value of each pixel, magnitude information about the gradient (step ST13).

Figure 7:
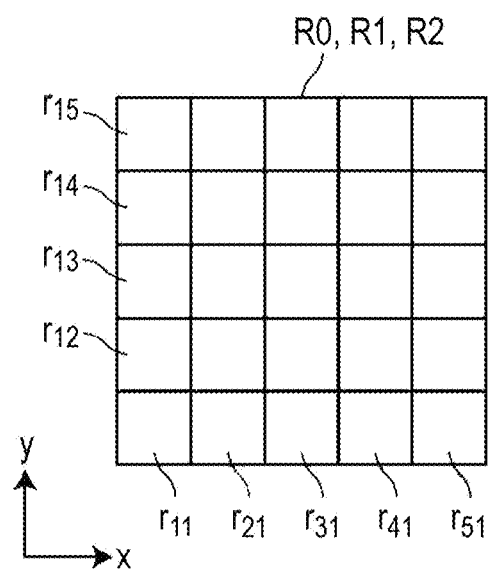
FIG. 7 is a diagram for describing magnitude information about a gradient.

FIG. 7 is a diagram for describing obtaining of magnitude information about a gradient. As illustrated in FIG. 7, the calculation target regions R0, R1, and R2 correspond to the predetermined defined region R, and therefore, the calculation target regions R0, R1, and R2 are regions of 5×5 pixels similar to the predetermined defined region R. In FIG. 7, the horizontal direction is represented by the x axis, the vertical direction is represented by the y axis, and each pixel in each of the calculation target regions R0, R1, and R2 is represented by $r_{xy}$.

For example, the selection unit 23 first obtains magnitude information about the gradient for each pixel $r_{xy}$ in the calculation target region R0 of the CT image G0. Specifically, the gradient vector is first calculated for each pixel $r_{xy}$ on the basis of expression (1) below.

$$G(x, y) = \frac{\partial I(x, y)}{\partial x} + \frac{\partial I(x, y)}{\partial y} \quad (1)$$

In expression (1) above, I(x, y) represents a function of a pixel of interest that is a target for which magnitude information about the gradient is obtained, and the first derivative of the function I(x, y) represents the vector quantity. G(x, y) represents the gradient vector and can be obtained as the sum of the derivative of the function I(x, y) in the x direction, that is, ∂I(x, y)/∂x, and the derivative thereof in the y direction, that is, ∂I(x, y)/∂y, as expressed by expression (1).

Next, the selection unit 23 obtains as magnitude information about the gradient, the absolute value of the gradient vector G(x, y), namely, ‖G(x, y)‖, on the basis of the gradient vector G(x, y) obtained using expression (1) above. The selection unit 23 also obtains magnitude information about the gradient for each pixel $r_{xy}$ in each of the calculation target regions R1 and R2 of the MR image G1 and the PET image G2 in a manner similar to the above.

Next, the selection unit 23 obtains the maximum value of the gradient magnitude for each of the calculation target regions R0, R1, and R2 on the basis of the magnitude information about the gradient obtained for each pixel in each of the calculation target regions R0, R1, and R2 of the CT image G0, the MR image G1, and the PET image G2 (step ST14).

Next, the selection unit 23 selects from among the CT image G0, the MR image G1, and the PET image G2, an image for which the obtained maximum value of the gradient magnitude is largest as an image for extracting a contour (step ST15). In this embodiment, the maximum value of the gradient magnitude obtained from the calculation target region R1 of the MR image G1 is largest among the CT image G0, the MR image G1, and the PET image G2, and therefore, the selection unit 23 selects the MR image G1 as an image for extracting a contour.

Note that the gradient magnitude indicates the degree of edge enhancement. An image having a higher degree of edge enhancement is stronger in contrast, and therefore, a contour is easily extracted. That is, an image for which the maximum value of the gradient magnitude is largest is an image for which the degree of edge enhancement is highest and an image from which a contour is easily extracted.

Referring back to FIG. 4, when the image selection process by the selection unit 23 is completed in step ST4, the contour extraction unit 24 subsequently extracts a contour from the selected image selected by the selection unit 23, that is, from the MR image G1 (step ST5).

Figure 8:
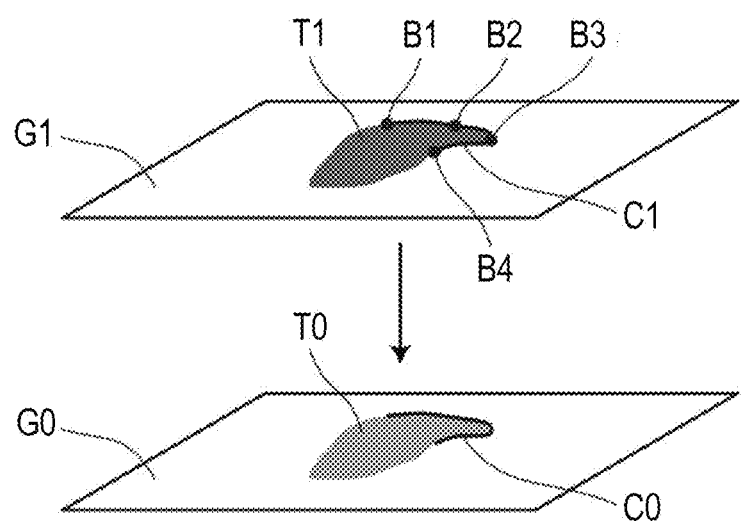
FIG. 8 is a diagram for describing extraction of a contour and creation of a contour.

FIG. 8 is a diagram for describing extraction of a contour and creation of a contour. Extraction of a contour is performed as illustrated in the upper part of FIG. 8. Specifically, the operator operates the input unit 15 to plot on the MR image G1, a plurality of control points B1, B2, B3, B4, . . . near the circumferential edge of a region T1 representing a tumor and an organ at risk that are targets of irradiation. The contour extraction unit 24 connects the control points along the circumferential edge of the region representing a tumor and an organ at risk that are targets of irradiation, on the basis of the plurality of plotted control points B1, B2, B3, B4, . . . to extract a contour C1.

Note that in order to make a description understandable, the contour C1 represents only part of the contour of the region T1 in FIG. 8; however, the contour C1 is actually the closed contour of the region T1. The contour extraction unit 24 saves position information about the contour extracted from the MR image G1 in the storage 13 as contour information.

Note that in this embodiment, a contour is extracted by the operator using a manual method; however, the present disclosure is not limited to this. As the method of extracting a contour, a method of automatically extracting a contour may be used or a publicly known technique may be used.

Next, the image processing unit 25 obtains from the storage 13 the contour information about the contour extracted from the MR image G1 by the contour extraction unit 24, and thereafter, reflects the contour information on the CT image G0 to generate a contour C0 on the CT image G0 as illustrated in the lower part of FIG. 8 (step ST6). Accordingly, the series of processes ends.

As described above, according to this embodiment, a process of accepting a specification of the position of the predetermined defined region R on the superimposed image G obtained by superimposing a plurality of images of different types including the CT image G0, which is a target on which a contour is created; selecting an image for extracting a contour on the basis of image information about the regions R0, R1, and R2, in the plurality of images of different types, each corresponding to the accepted predetermined defined region R; and extracting the contour from the selected image is performed. Accordingly, an optimum image for extracting a contour can be automatically selected from the superimposed image G obtained by superimposing the plurality of images. Therefore, a contour can be precisely and efficiently created on the basis of the features of the respective images.

Note that in the above-described embodiment, the defined region for which a specification of its position is accepted by the accepting unit 22 has a predetermined size; however, the present disclosure is not limited to this. The accepting unit 22 may change the size of the defined region on the basis of the type of imaging target in the plurality of images including the target image G0. For example, as an organ in an image is larger, the defined region is made larger, and as an organ in an image is smaller, the defined region is made smaller. Accordingly, the accuracy of selection of an image by the selection unit 23 can be increased. Note that the type of organ can be obtained from information attached to the image accepted by the accepting unit 22.

Further, in the above-described embodiment, the accepting unit 22 accepts one predetermined defined region R; however, the present disclosure is not limited to this, and the accepting unit 22 may accept a plurality of defined regions R. In this case, it is preferable that the plurality of defined regions R be set at different positions. For each of the plurality of defined regions R, the selection unit 23 selects an image for extracting a contour as in the above-described embodiment, and the selection unit 23 selects as an image for extracting a contour, an image that is selected a largest number of times for the plurality of defined regions R.

Further, in the above-described embodiment, the target image is the CT image G0 and the plurality of images are the CT image G0, the MR image G1, and the PET image G2; however, the present disclosure is not limited to this, and the plurality of images may include, for example, only the CT image G0 and the MR image G1. The plurality of images of different types need to include at least a target image and may be a combination of any images. Further, the target image is not limited to the CT image G0 and may be an image obtained by imaging based on any other imaging principle.

Further, in the above-described embodiment, the selection unit 23 selects an image for extracting a contour on the basis of magnitude information about the gradient specifically by using expression (1) above; however, the present disclosure is not limited to this, and a publicly known derivative filter or a publicly known expression for calculating the degree of edge enhancement can be used.

The present disclosure is not limited to the above-described embodiment, and changes can be made as appropriate without departing from the spirit of the present disclosure.

REFERENCE SIGNS LIST

1 diagnostic imaging support apparatus
2 three-dimensional imaging apparatus
3 image storage server
4 network
11 CPU
12 memory
13 storage
14 display
15 input unit
21 image obtaining unit
22 accepting unit
23 selection unit
24 contour extraction unit
25 image processing unit
G superimposed image
G0 CT image (target image)
G1 MR image
G2 PET image
A cursor
A0, A1, A2 specified position
R defined region
R0, R1, R2 calculation target region
T0, T1, T2 region
$r_{xy}$ pixel
B1, B2, B3, B4 control point
C0, C1 contour

What is claimed is:

1. A diagnostic imaging support apparatus comprising:
a processor configured to:
accept a specification of a position of a predetermined defined region on a superimposed image obtained by superimposing a plurality of images of different types including a target image that is a target on which a contour is created;
select an image for extracting a contour on the basis of image information about regions according to a magnitude information about a gradient of each pixel in each of the regions, in the plurality of images of different types, each corresponding to the accepted predetermined defined region; and
extract the contour from the selected image.

2. The diagnostic imaging support apparatus according to claim 1, wherein the processor is further configured to create a contour by reflecting contour information about the extracted contour in the target image.

3. The diagnostic imaging support apparatus according to claim 2, wherein the processor selects on the basis of the magnitude information about the gradient of the each pixel in each of the regions, an image in which the gradient is largest.

4. The diagnostic imaging support apparatus according to claim 3, wherein the processor is configured to:
obtain the magnitude information about the gradient from the image information about the each pixel in the regions, in the plurality of images of different types, each corresponding to the predetermined defined region;
obtain a maximum value from the magnitude information about the gradient of the each pixel for each of the plurality of images of different types; and
select the image for which the obtained maximum value is largest from among the plurality of images.

5. The diagnostic imaging support apparatus according to claim 2, wherein the processor is configured to change a size of the predetermined defined region on the basis of a type of an imaging target in the plurality of images of different types.

6. The diagnostic imaging support apparatus according to claim 2, wherein the plurality of images of different types are a plurality of images obtained under different imaging conditions.

7. The diagnostic imaging support apparatus according to claim 2, wherein the plurality of images of different types are a plurality of images obtained on the basis of different imaging principles.

8. The diagnostic imaging support apparatus according to claim 2, wherein the plurality of images of different types are a plurality of images obtained under different imaging conditions and a plurality of images obtained on the basis of different imaging principles.

9. The diagnostic imaging support apparatus according to claim 1, wherein the processor is configured to select on the basis of the magnitude information about the gradient of the each pixel in each of the regions, an image in which the gradient is largest.

10. The diagnostic imaging support apparatus according to claim 9, wherein the processor is configured to:
obtain the magnitude information about the gradient from the image information about the each pixel in the regions, in the plurality of images of different types, each corresponding to the predetermined defined region;
obtain a maximum value from the magnitude information about the gradient of the each pixel for each of the plurality of images of different types; and
select the image for which the obtained maximum value is largest from among the plurality of images.

11. The diagnostic imaging support apparatus according to claim 1, wherein the processor is configured to change a size of the predetermined defined region on the basis of a type of an imaging target in the plurality of images of different types.

12. The diagnostic imaging support apparatus according to claim 1, wherein the plurality of images of different types are a plurality of images obtained under different imaging conditions.

13. The diagnostic imaging support apparatus according to claim 12, wherein the plurality of images of different types are images of one type, which are CT images, MR images, or PET images.

14. The diagnostic imaging support apparatus according to claim 1, wherein the plurality of images of different types are a plurality of images obtained on the basis of different imaging principles.

15. The diagnostic imaging support apparatus according to claim 14, wherein the plurality of images of different types are images of two or more types among a CT image, an MR image, and a PET image.

16. The diagnostic imaging support apparatus according to claim 1, wherein the plurality of images of different types are a plurality of images obtained under different imaging conditions and a plurality of images obtained on the basis of different imaging principles.

17. The diagnostic imaging support apparatus according to claim 1, wherein the target image is a CT image.

18. The diagnostic imaging support apparatus according to claim 1, wherein the plurality of images of different types are cross-sectional images in a same direction.

19. A diagnostic imaging support method comprising:
accepting a specification of a position of a predetermined defined region on a superimposed image obtained by superimposing a plurality of images of different types including a target image that is a target on which a contour is created;
selecting an image for extracting a contour on the basis of image information about regions according to a magnitude information about a gradient of each pixel in each of the regions, in the plurality of images of different types, each corresponding to the accepted predetermined defined region; and
extracting the contour from the selected image.

20. A non-transitory computer readable recording medium storing a diagnostic imaging support program for causing a computer to perform a process comprising:
a step of accepting a specification of a position of a predetermined defined region on a superimposed image obtained by superimposing a plurality of images of different types including a target image that is a target on which a contour is created;
a step of selecting an image for extracting a contour on the basis of image information about regions according to a magnitude information about a gradient of each pixel in each of the regions, in the plurality of images of different types, each corresponding to the accepted predetermined defined region; and
a step of extracting the contour from the selected image.

* * * * *